United States Patent [19]

Schenk

[11] Patent Number: Plant 7,428

[45] Date of Patent: Jan. 22, 1991

[54] LILY PLANT NAMED DAME BLANCHE

[75] Inventor: Pieter C. Schenk, Medemblik, Netherlands

[73] Assignee: H.J.A. Rooijakkers B.V., Netherlands

[21] Appl. No.: 481,065

[22] Filed: Feb. 16, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct lily plant named Dame Blanche characterized by its pure white tepal color, reddish-brown anthers, floriferous habit, relatively short and strong stems, and vigorous growth habit.

1 Drawing Sheet

The present invention comprises a new and distinct cultivar of lily, botanically known as *Lilium oriental* hybriden and hereinafter referred to by the cultivar name Dame Blanche.

Dame Blanche was originated from a hybridization made by the inventor Pieter C. Schenk in a controlled breeding program in Wieringerwerf, The Netherlands in 1980. The female parent was a cultivar of *Lilium oriental* hybriden named Merci. The male parent of Dame Blanche was an unnamed cultivar of *Lilium oriental* hybriden.

Dame Blanche was discovered and selected as one flowering plant within the progeny of the stated cross by Pieter C. Schenk in May 1982 in a controlled environment in Wieringerwerf, The Netherlands.

The first act of asexual reproduction of Dame Blanche was accomplished by Pieter C. Schenk when small bulbs were taken from the bulb of the initial selection in November 1982 in a controlled environment in Wieringerwerf, The Netherlands. Horticultural examination of selected units initiated Oct. 5, 1987 and continuing to Apr. 18, 1989 has demonstrated that the combination of characteristics as herein disclosed for Dame Blanche are firmly fixed and are retained through successive generations of asexual reproduction.

Dame Blanche has not been observed under all possible environmental conditions. The phenotype may vary significantly with variations in environment such as temperature, light intensity, and day length. The following observations, measurements, and comparisons describe plants grown in Wageningen, The Netherlands under greenhouse conditions which approximate those generally used in commercial practice.

The following traits have been repeatedly observed and are determined to be basic characteristics of Dame Blanche which in combination distinguish this lily as a new and distinct cultivar.

1. Pure white tepal color.
2. Floriferous habit.
3. Upright flower buds.
4. Relatively short and strong stems.
5. A relatively short forcing period.
6. Strong and vigorous growth habit.
7. Red to reddish brown anthers which provide a highly pleasing contrast with the pure white tepals.

Of the many cultivars known to the present inventor, the most similar in comparison to Dame Blanche is the *Lilium oriental* hybrid cultivar Casa Blanca, a cultivar also having white tepals. In comparison to Casa Blanca, Dame Blanche has more upright flower buds, a quicker forcing period, stronger and shorter stems, and produces more flowers.

The accompanying photographic drawing shows typical flower and foliage characteristics of Dame Blanche, with colors being as true as possible with illustrations of this type.

In the following description, color references are made to The Royal Horticultural Society Colour Chart. The color values were determined at Wageningen, The Netherlands.

Origin: Seedling from breeding program.

Parentage:

*Seed parent.*—Merci.

*Pollen parent.*—Unnamed seedling of a *Lilium oriental* hybriden cultivar.

Classification:

*Botanic.*—*Lilium oriental* hybriden.

*Commercial.*—Dame Blanche.

The Plant:

*Form.*—A single stem carrying numerous pedicels alternately arranged.

*Height.*—On opening of anthers of first flower, 70 to 120 cm. (low to medium).

*Growth habit.*—Vigorous and strong.

*Stem.*—Circular in transverse section, internodal length uniform, light to medium green with anthocyanin pigmentation present.

*Foliage.*—Quantity: From 20 to 45 leaves depending on growing conditions. Size of leaf: Mature leaves are 16–22 cm. long and 2–4 cm. wide. Shape of leaf: Generally ovate to elliptical, tip acuminate, base of leaf forming acute angle of approximately 30° with stem. Texture: Smooth. Color: Medium green.

*Bulbs.*—Size: Outlet 6 to 24 cm. (12 to 24 cm. is full size). Color: White.

The Bud:

*Form.*—Tapering (like a lancet).

*Size.*—10 to 17 cm. in length.

*Opening.*—Unfolds normally.

*Color.*—Green 138A-B when very immature, maturing first to approximately 147D and then toward white prior to opening.

*Tepals.*—Folded, three visible.

The flower:

*Blooming habit.*—Raceme.

*Size.*—20 to 25 cm. in total diameter.

*Borne.*—Upright to horizontal.

*Shape.*—Generally in form of hexagonal star; bowl-shaped in cross-section, with tips bent downwardly; tepal margins sinuated.

*Tepalage.*—Number of tepals: Six. Arrangement: Three inner and three outer. Color: Upper surface: Pure white, not represented in 155A–D; median rib near 155A. Lower surface: Pure White, not represented in 155A–D; median rib near 155A. Tepal longevity: Two or three weeks in vase; three to five weeks in soil with bulb. Spotting or marking: None.

*Pedicel.*—Length: 10 to 15 cm. Color: Green. Form: Slightly curved.

*Texture.*—Papillose, pronounced on inner surface of tepals.

*Disease resistance.*—No disease problems noted to date.

*Fragrance.*—Yes.

*Lasting quality.*—Excellent.

Reproductive organs:

*Stamens, anthers.*—Arrangement: Anthers form a generally circular pattern at their upper ends. Length 2 to 3 cm. Number: Six. Filaments: Long and light green in color.

*Pollen color.*—Orange.

*Anther color.*—Red to red-brown, approximately between 145A and 179A.

*Pistils.*—One, long and green.

*Stigma.*—Triangular and purple.

*Ovaries.*—Triangular in shape.

I claim:

1. A new and distinct cultivar of lily plant named Dame Blanche, as illustrated and described.

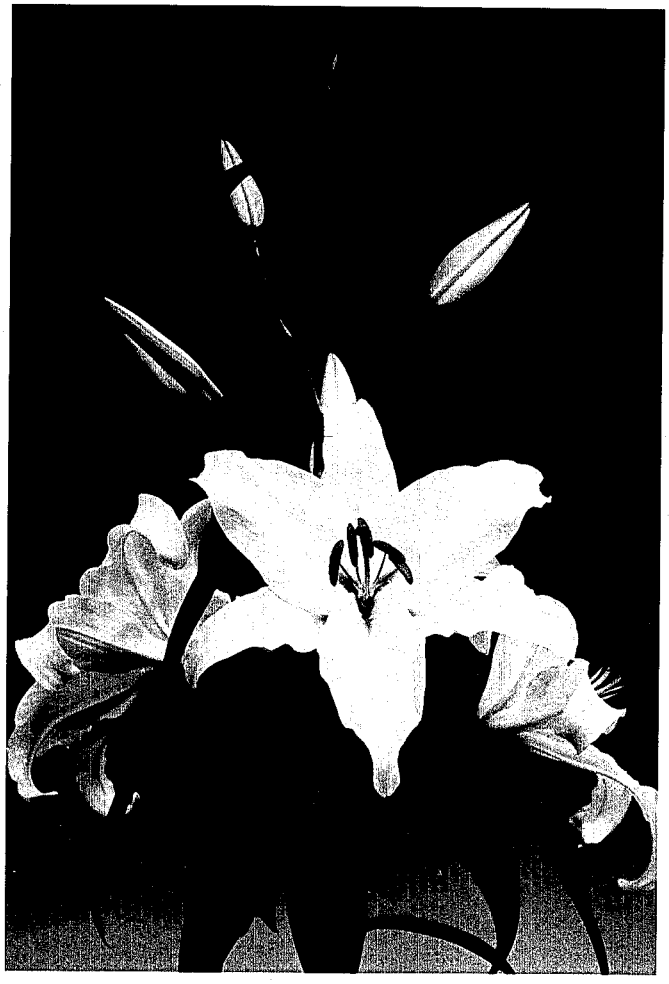

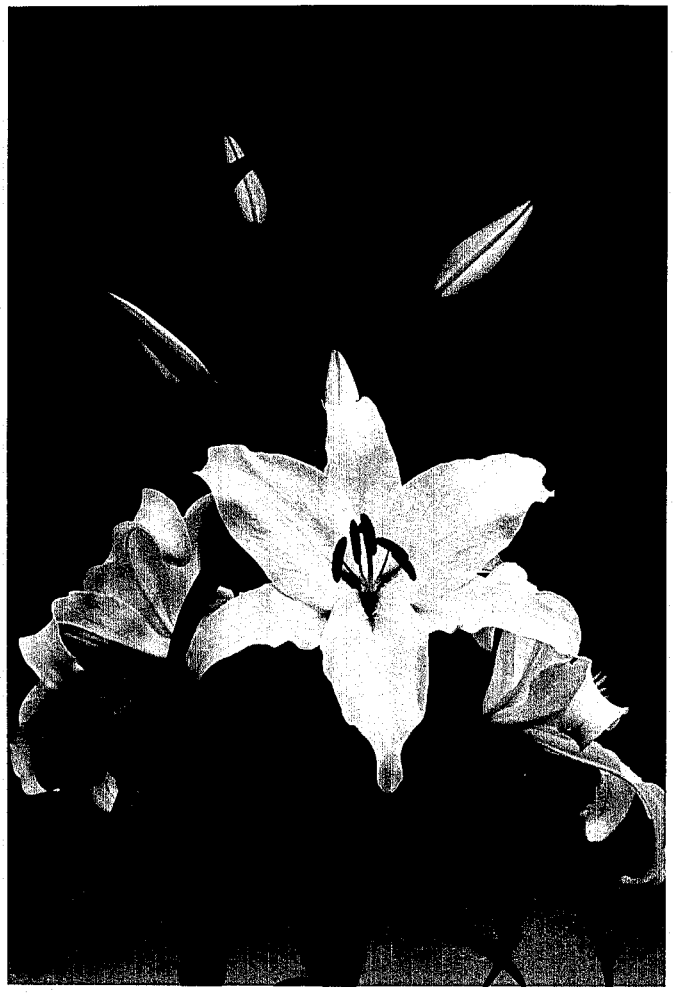

* * * * *